(12) United States Patent
Iwama et al.

(10) Patent No.: US 11,549,938 B2
(45) Date of Patent: Jan. 10, 2023

(54) ANALYSIS UNIT, WASHING DEVICE, AND WASHING METHOD

(71) Applicant: JVCKENWOOD Corporation, Yokohama (JP)

(72) Inventors: Shigehiko Iwama, Yokohama (JP); Yuichi Hasegawa, Yokohama (JP); Koji Tsujita, Yokohama (JP); Masayuki Ono, Yokohama (JP); Katsue Horikoshi, Yokohama (JP); Atsushi Saito, Yokohama (JP)

(73) Assignee: JVCKENWOOD CORPORATION, Yokohama (JP)

( * ) Notice: Subject to any disclaimer, the term of this patent is extended or adjusted under 35 U.S.C. 154(b) by 146 days.

(21) Appl. No.: 16/797,270

(22) Filed: Feb. 21, 2020

(65) Prior Publication Data

US 2020/0284784 A1 Sep. 10, 2020

(30) Foreign Application Priority Data

Mar. 6, 2019 (JP) .............................. JP2019-040403

(51) Int. Cl.
*G01N 33/543* (2006.01)
*G01N 33/53* (2006.01)
*B01L 3/00* (2006.01)

(52) U.S. Cl.
CPC .... *G01N 33/5304* (2013.01); *B01L 3/502715* (2013.01); *G01N 33/54366* (2013.01);
(Continued)

(58) Field of Classification Search
CPC ........ B01L 3/502715; B01L 3/00; B01L 3/50; B01L 3/502; B01L 3/5085; B01L 2200/0642; B01L 2200/16; B01L 2200/025; B01L 2200/0631; B01L 2300/0636; B01L 2300/0803; B01L 2300/0829; B01L 2300/0858; G01N 33/54366;
(Continued)

(56) References Cited

U.S. PATENT DOCUMENTS

| | | | | |
|---|---|---|---|---|
| 4,681,742 | A * | 7/1987 | Johnson ................ | B01L 3/5085 422/552 |
| 2007/0148649 | A1* | 6/2007 | Shigesada .............. | B01D 63/08 435/6.12 |
| 2016/0033486 | A1* | 2/2016 | Itonaga ................ | G01N 33/487 435/287.2 |

FOREIGN PATENT DOCUMENTS

| JP | 2007132882 A | 5/2007 |
|---|---|---|
| JP | 2012013697 A | 1/2012 |

(Continued)

OTHER PUBLICATIONS

Official Action dated May 24, 2022 in the counterpart Japanese application No. 2019-040403.

*Primary Examiner* — Melanie Brown
*Assistant Examiner* — Jennifer H. Tieu
(74) *Attorney, Agent, or Firm* — Nath, Goldberg & Meyer; Jerald L. Meyer

(57) ABSTRACT

An analysis unit for quantitating detection target substances bound to antibodies includes wells and inclination parts. The wells each have a hole-like shape defined by an opening, an inner circumferential surface, and a bottom. The inclination parts each have an inclined surface connected to the inner circumferential surface and inclined downward such that whose height with respect to the bottom decreases as a distance from an outer circumferential side of the well increases.

3 Claims, 10 Drawing Sheets

(52) U.S. Cl.
CPC ............... *G01N 33/54393* (2013.01); *B01L 2200/0642* (2013.01); *B01L 2200/16* (2013.01)

(58) Field of Classification Search
CPC ............ G01N 33/54393; G01N 35/10; G01N 35/1004; G01N 33/5304
See application file for complete search history.

(56) References Cited

FOREIGN PATENT DOCUMENTS

| | | |
|---|---|---|
| JP | 2015-127691 A | 7/2015 |
| WO | 2017082195 A1 | 5/2017 |
| WO | WO-2018109008 A1 * | 6/2018 ........ B01L 3/502761 |

* cited by examiner

ANALYSIS UNIT, WASHING DEVICE, AND WASHING METHOD

CROSS REFERENCE TO RELATED APPLICATION

This application is based upon and claims the benefit of priority under 35 U.S.C. § 119 from Japanese Patent Application No. 2019-040403 filed on Mar. 6, 2019, the entire contents of which are incorporated herein by reference.

BACKGROUND

The present disclosure relates to an analysis unit, a washing device, and a washing method.

Immunoassays are known that quantitatively analyze disease detection and therapeutic effects by detecting particular antigens or antibodies as specimens associated with diseases. Japanese Unexamined Patent Application Publication No. 2015-127691 (Patent Document 1) discloses an analysis method of fixing antibodies to an analysis substrate in an analysis unit including a plurality of wells, allowing the antibodies to bind to detection target substances, binding the detection target substances to nanoparticles, and counting the number of the nanoparticles, so as to quantitate the detection target substances.

In particular, a buffer solution including antibodies is injected into the wells and then incubated, so as to fix the antibodies to the analysis substrate. After the antibodies are fixed, the excessive buffer solution is sucked by a suction nozzle, and the wells are cleaned with a cleaning solution. The cleaning solution is then sucked with the suction nozzle to dry the wells, and a sample solution including detection target substances is injected to the wells and then incubated, so as to bind the detection target substances to the antibodies.

The sample solution including the detection target substances is then sucked with the suction nozzle, and the wells are cleaned again with a cleaning solution. The cleaning solution is sucked with the suction nozzle to dry the wells, and a buffer solution including nanoparticles is injected to the wells and then incubated, so as to bind the nanoparticles to the detection target substances.

The buffer solution including the nanoparticles is then sucked with the suction nozzle, and the wells are cleaned again with a cleaning solution. The cleaning solution is sucked with the suction nozzle to dry the wells. The analysis substrate thus can be prepared through the above process on which the detection target substances sandwiched between the nanoparticles and the antibodies are captured.

SUMMARY

The washing step disclosed in Patent Document 1 may have a problem with residues (substances excluding the detection target included in the sample solution or nanoparticles not bound to the detection target) remaining in the wells if the cleaning solution dispensed from a dispensing nozzle is sucked with the suction nozzle before not being sufficiently mixed with the solution used in the preceding step (such as the buffer solution or the sample solution), leading to insufficient washing. A method is known that increases a flow rate of the cleaning solution so as to be mixed sufficiently with the solution used in the preceding step in order to improve the effect of washing when the washing is not sufficient. The increase in the flow rate of the cleaning solution during washing after the nanoparticles are bound to the detection target substances, however, may lead the nanoparticles to come off the detection target substances due to the flow of the cleaning solution.

A first aspect of one or more embodiments provides an analysis unit for quantitating detection target substances bound to antibodies, the analysis unit including: a well having a hole-like shape defined by an opening, an inner circumferential surface, and a bottom; and an inclination part having an inclined surface connected to the inner circumferential surface and inclined downward such that whose height with respect to the bottom decreases as a distance from an outer circumferential side of the well increases.

A second aspect of one or more embodiments provides a washing device including: a stage on which the analysis unit according to the first aspect is mounted; a dispensing nozzle from which a solution is injected to the well; and a controller configured to control the stage or the dispensing nozzle so as to bring the dispensing nozzle to be closer to or away from the inclined surface, and control the dispensing nozzle to dispense the solution to the inclined surface.

A third aspect of one or more embodiments provides a washing method including: causing a controller to control a stage on which an analysis unit is mounted, the analysis unit including a well having a hole-like shape defined by an opening, an inner circumferential surface, and a bottom, and an inclination part having an inclined surface connected to the inner circumferential surface and inclined downward such that whose height with respect to the bottom decreases as a distance from an outer circumferential side of the well increases, so as to bring a dispensing nozzle to be located over the inclination part of the analysis unit; causing the controller to control the dispensing nozzle so as to dispense a solution to the inclination part; and causing the controller to control a suction nozzle so as to suck the solution flowing into the well through the inclination part.

DETAILED DESCRIPTION

[Analysis Unit]

Figure 1:
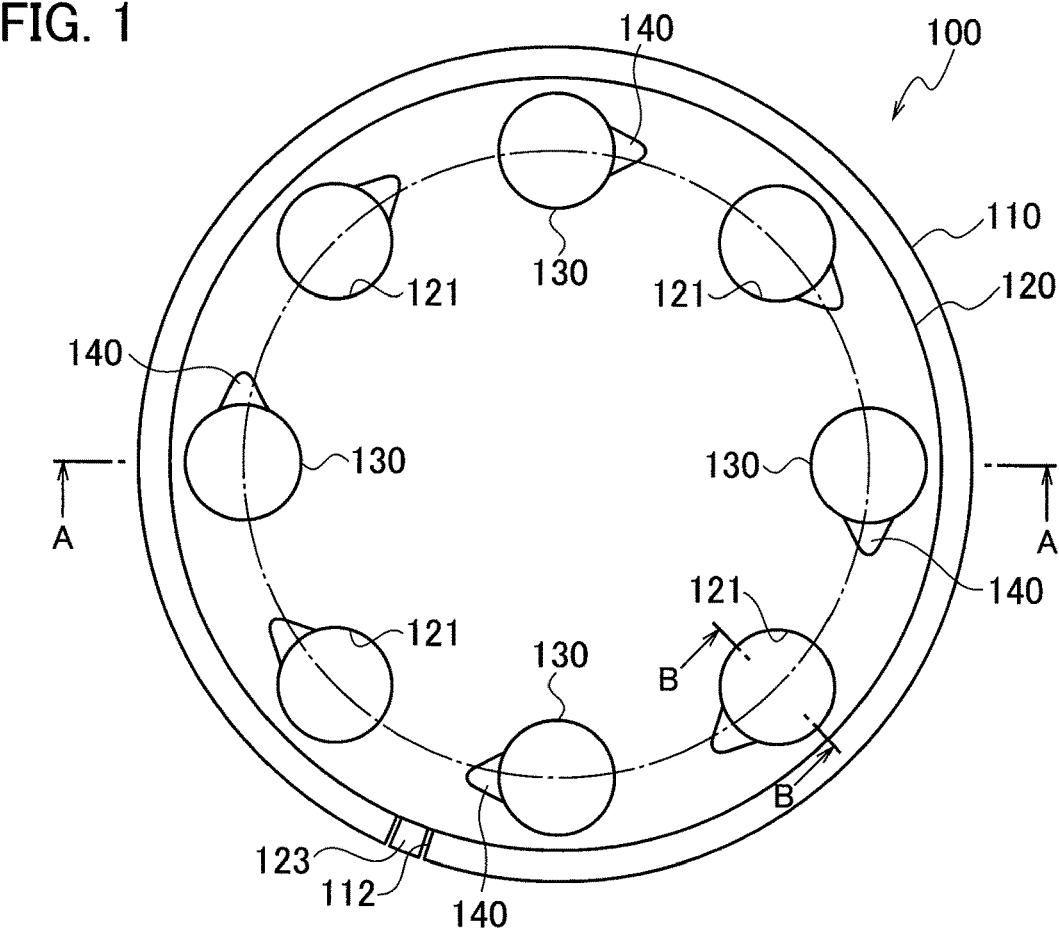
FIG. 1 is a plan view illustrating a configuration of an analysis unit according to one or more embodiments.
Figure 2A:
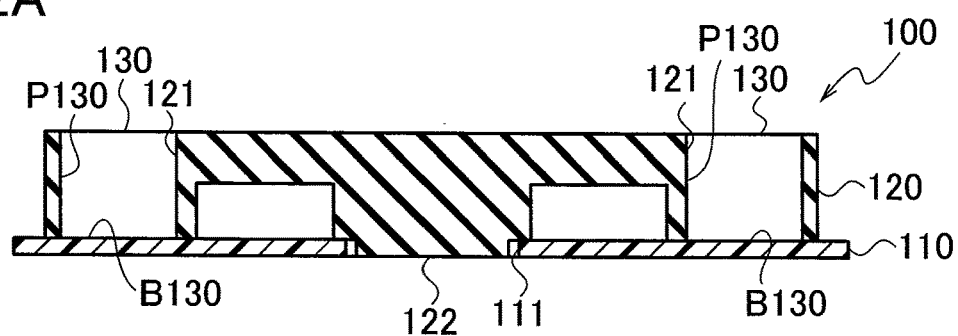
FIG. 2A is a cross-sectional view of the analysis unit taken along line A-A in FIG. 1.
Figure 2B:
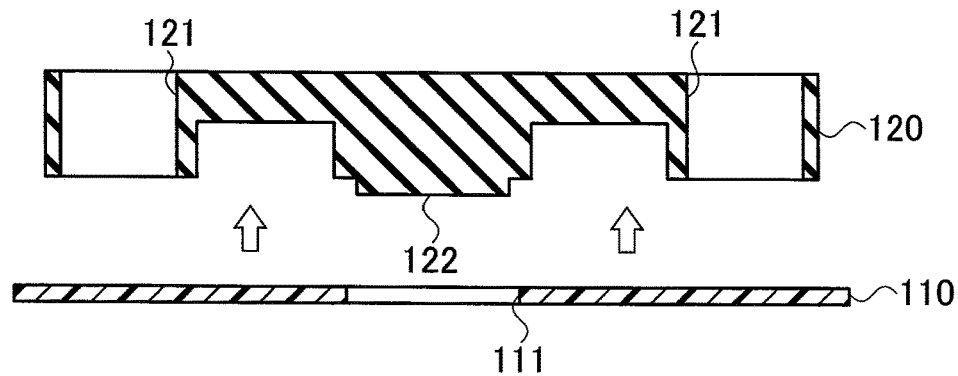
FIG. 2B is a cross-sectional view illustrating a state in which a cartridge is removed from an analysis substrate.
Figure 4:
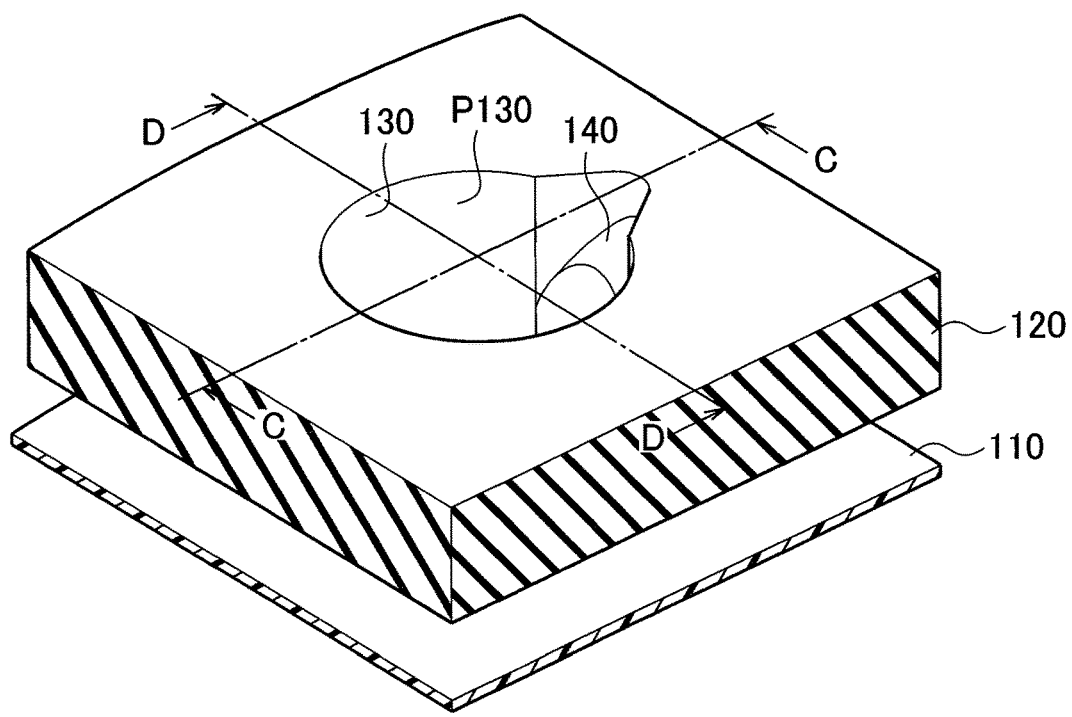
FIG. 4 is an enlarged perspective view showing the well.
Figure 5:
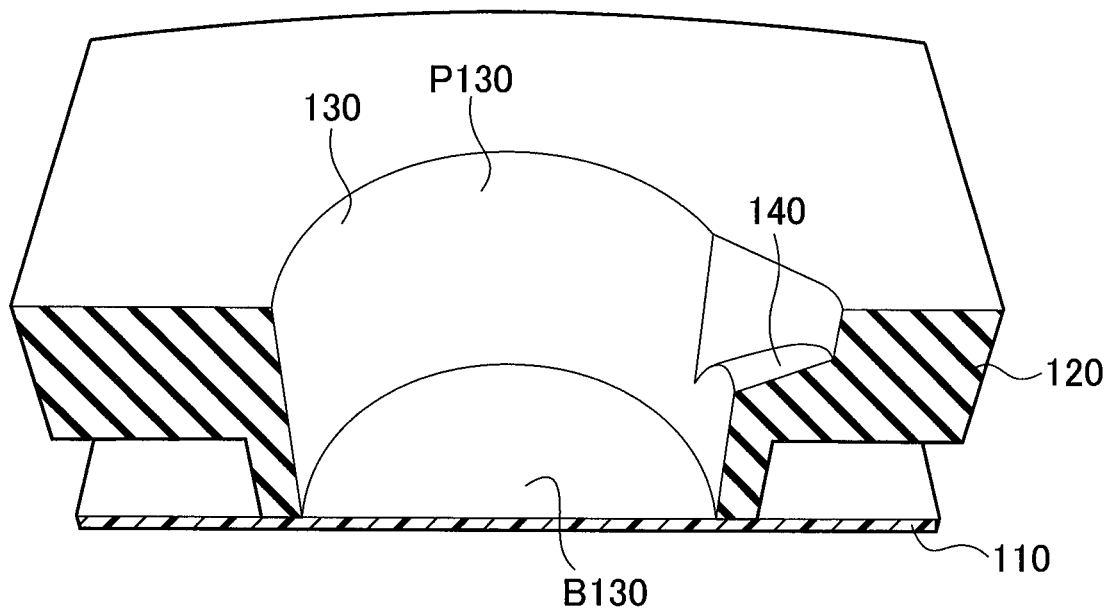
FIG. 5 is an enlarged perspective view showing the well cross-sectioned along line C-C in FIG. 4.
Figure 6:
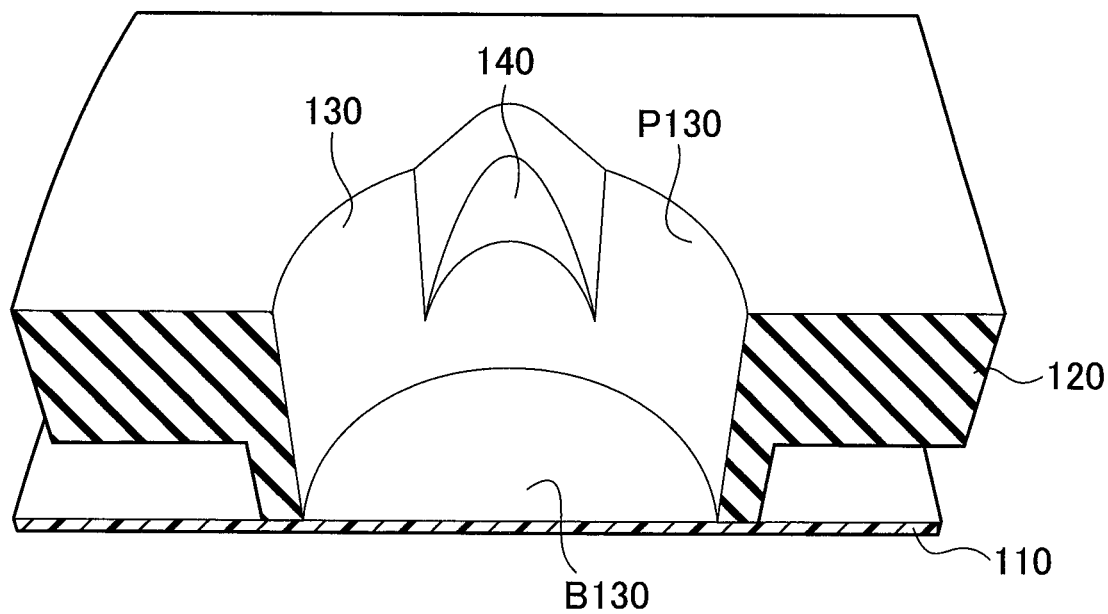
FIG. 6 is an enlarged perspective view showing the well cross-sectioned along line D-D in FIG. 4.

An analysis unit according to one or more embodiments is described below with reference to FIG. 1 to FIG. 6. FIG. 1 is a plan view showing the analysis unit according to one or more embodiments as viewed from the side on which a cartridge is arranged. FIG. 2A is a cross-sectional view of the analysis unit taken along line A-A in FIG. 1. FIG. 2B is a cross-sectional view illustrating a state in which the cartridge is removed from an analysis substrate. FIG. 4 is a partly enlarged view of the well shown in FIG. 1. FIG. 5 is a view of the well cross-sectioned along line C-C in FIG. 4. FIG. 6 is a view of the well cross-sectioned along line D-D in FIG. 4.

As shown in FIG. 1, the analysis unit 100 for quantitating detection target substances including particular antigens includes the analysis substrate 110 and the cartridge 120. The analysis substrate 110 is formed into a circular shape equivalent to optical discs such as Blu-ray discs (BDs), DVDs, and compact discs (CDs).

The analysis substrate 110 is formed of resin material such as polycarbonate resin and cycloolefin polymer, commonly used for optical discs. The analysis substrate 110 is not limited to the optical discs described above, and may be any optical disc having other forms or conforming to prescribed standards.

As shown in FIG. 1, FIG. 2A, or FIG. 2B, the analysis substrate 110 has a center hole 111 and a slit 112. The center hole 111 is formed in the middle of the analysis substrate 110. The slit 112 is formed at the circumferential edge of the analysis substrate 110. The slit 112 serves as a reference position-defining portion for defining a reference position of the analysis substrate 110 in the rotating direction.

As shown in FIG. 1, FIG. 2A, or FIG. 2B, the cartridge 120 is provided with a plurality of cylindrical penetration holes 121 arranged along the circumferential direction. The penetration holes 121 are arranged at regular intervals such that the respective center points are located on the common circle. The cartridge 120 includes a projection 122 in the middle and a projection 123 at the circumferential edge.

When attaching the cartridge 120 to the analysis substrate 110, the operator inserts the projection 122 into the center hole 111 of the analysis substrate 110, and inserts the projection 123 into the slit 112, so that the cartridge 120 and the analysis substrate 110 are fitted to each other.

Figure 3:
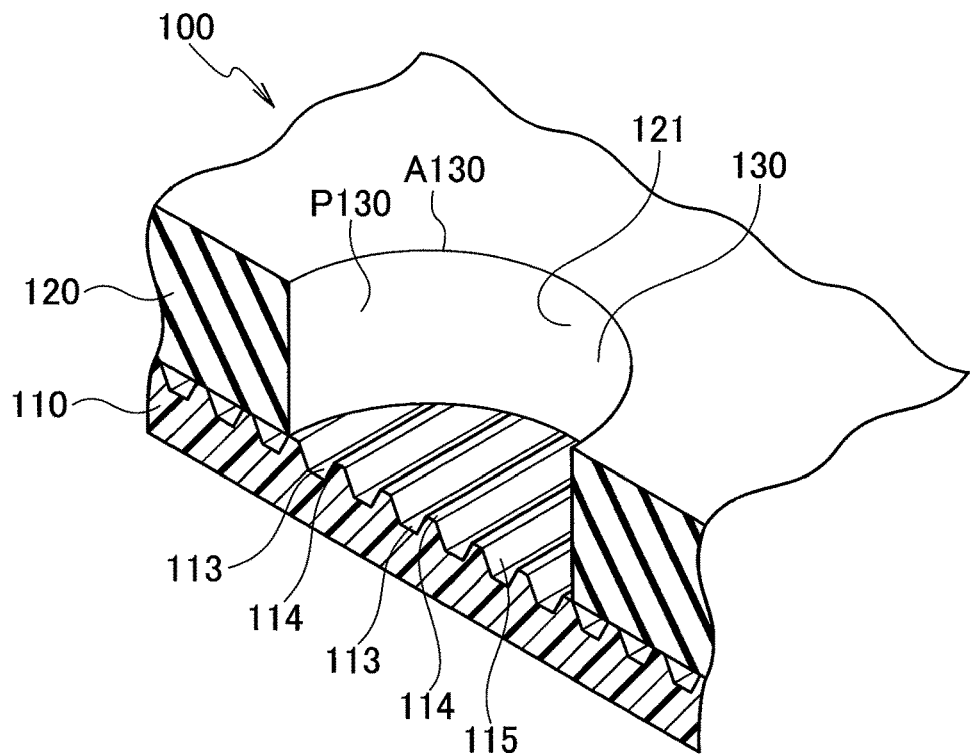
FIG. 3 is an enlarged perspective view showing a well cross-sectioned along line B-B in FIG. 1.

As shown in FIG. 2A or FIG. 3, the analysis unit 100 includes a plurality of wells 130 defined by the penetration holes 121 of the cartridge 120 and the surface (track regions 115) of the analysis substrate 110. The track regions 115 are provided with convex portions 114 and recesses 113 alternately arranged. The wells 130 each have a hole-like shape defined by an opening A130, an inner circumferential surface P130, and a bottom B130. The surface of the analysis substrate 110 serves as the bottom B130 of the respective wells 130. An inner circumferential surface on the inner side of each penetration hole 121 corresponds to the inner circumferential surface P130 of each well 130. The respective wells 130 are arranged at regular intervals such that the respective center points are located on the common circle. The cartridge 120 is thus provided with plural pairs of the opening A130 and the inner circumferential surface P130.

The opening A130 is provided on the cartridge 120 on the surface on the opposite side of the bottom B130. The wells 130 each serve as a holder for storing a solution such as a sample solution, a buffer solution, and a cleaning solution. While FIG. 1 illustrates the eight wells 130, the number of the wells 130 is not limited to eight.

As shown in FIG. 2B, the cartridge 120 is detachable from the analysis substrate 110. Nanoparticles for labeling detection target substances are detected and measured only by use of the analysis substrate 110 away from the cartridge 120.

As shown in FIG. 1 and FIG. 4 to FIG. 6, the analysis unit 100 is provided with an inclination part 140 continuously connected to the well 130 (in particular, to the inner circumferential surface of the well 130). The inclination part 140 is formed to continuously extend to the penetration hole 121 of the cartridge 120 (in particular, to the inner circumferential surface of the cartridge 121). The inclination part 140 is located toward the opening A130, and is inclined to the bottom B130 of the well 130. FIG. 1 illustrates the case in which the respective inclination parts 140 are arranged at regular intervals in the same circumferential direction such that the respective middles are located on the common circle.

The inclination part 140 has an inclined surface inclined to the bottom B130 of the well 130 in the radial direction of the well 130. In particular, the inclined surface of the inclination part 140 is inclined downward such that the height with respect to the bottom B130 decreases from a part on the outer side of the opening A130 as viewed from the middle of the well 130. Namely, the height with respect to the bottom B130 decreases as a distance from the outer circumferential side of the well 130 increases. FIG. 4 to FIG. 6 illustrate the inclined surface inclined from the outer circumferential side of the well 130 toward the middle of the bottom B130. The inclined surface may have any inclination pattern from the outer circumferential side toward the bottom B130, which is either entirely uniform or varies depending on the position.

The inclined surface is inclined to the bottom B130 of the well 130 in the circumferential direction of the inner circumferential surface P130 of the well 130. In particular, the inclined surface is a saddle-like surface (saddle-like portion) inclined to be closer to the bottom B130 of the well 130 as the inclined surface is away from the middle at the connection part between the inclination part 140 and the opening A130 in the circumferential direction of the well 130. As illustrated in FIG. 4 to FIG. 6, the saddle-like portion has a surface inclined downward such that the height continuously decreases toward the bottom B130 of the well 130 as the inclined surface is away from the middle in the circumferential direction of the well 130. The saddle-like portion may have any inclination pattern of the surface that is closer to the bottom B130 in association with the separation from the middle in the circumferential direction of the well 130, and may vary depending on the position. The saddle-like portion may have a surface uniformly inclined to the bottom B130 together with the separation from the middle in the circumferential direction of the well 130.

As shown in FIG. 6, the inclination part 140 has a symmetrical shape in the circumferential direction of the well 130. The inclination part 140 has a width which varies in the radial direction of the well 130. In particular, the width of the inclination part 140 increases in the direction from the outer circumference to the middle of the well 130. FIG. 4 to FIG. 6 illustrate the width of the inclination part 140 continuously increasing from the outer circumference toward the middle of the well 130. The width of the inclination part 140 toward the middle of the well 130 is equal to or smaller than the diameter of the well 130 (the insertion hole 121).

[Washing Device]

Figure 7:
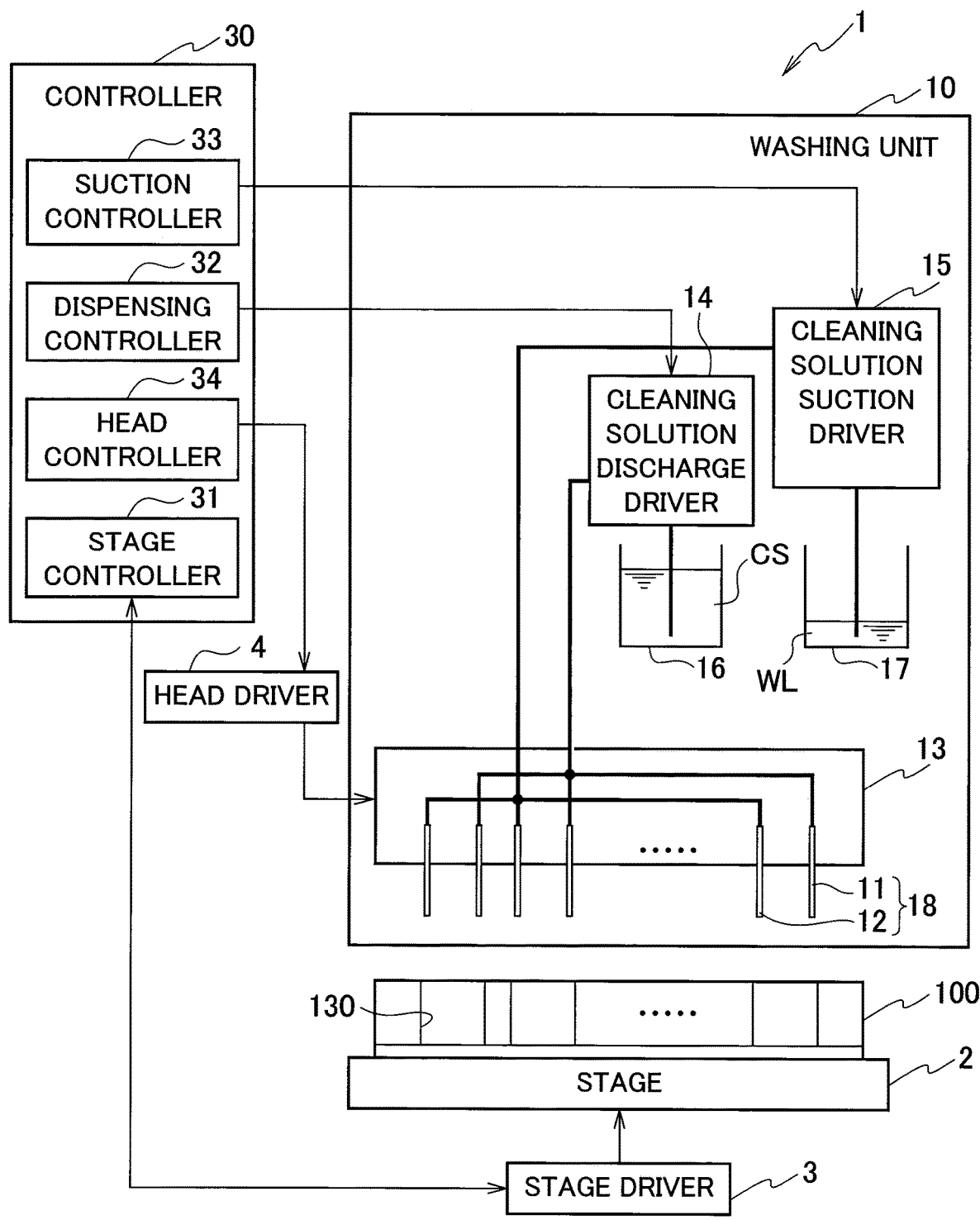
FIG. 7 is a configuration diagram illustrating a washing device according to one or more embodiments.

A washing device according to one or more embodiments is described below with reference to FIG. 7. FIG. 7 is a configuration diagram illustrating the washing device 1 according to one or more embodiments. The washing device 1 includes a stage 2, a stage driver 3, a washing unit 10, and a controller 30. The washing unit 10 includes a dispensing nozzle 11, a suction nozzle, 12, a nozzle head 13, a cleaning solution dispensing driver 14, a cleaning solution suction driver 15, a cleaning solution container 16, and a waste liquid container 17.

The dispensing nozzle 11 and the suction nozzle 12 are fixed to the nozzle head 13. A set of the dispensing nozzle 11 and the suction nozzle 12 implements a nozzle unit 18. When the analysis unit 100 includes the eight wells 130 as illustrated in FIG. 1, eight nozzle units 18 corresponding to the eight wells 130 are fixed to the nozzle head 13.

The controller 30 includes a stage controller 31, a dispensing controller 32, and a suction controller 33. The controller 30 may be a computer device or a central processing unit (CPU). The analysis unit 100 is mounted on the stage 2 with the wells 130 and the nozzle units 18 aligned with each other.

The stage controller 31 controls the stage driver 3 so as to bring the stage 2 to be closer to or away from the nozzle head 13. When the analysis unit 100 is mounted on the stage 2, the stage controller 31 controls the stage driver 3 so as to bring the analysis unit 100 to be closer to or away from the nozzle head 13.

The stage controller 31 controls the stage driver 3 so as to allow the stage 2 to rotate at a predetermined angle in a first rotating direction or to rotate in a second direction opposite to the first rotating direction. The stage controller 31 can allow the analysis unit 100 mounted on the stage 2 to rotate at a predetermined angle in the first or second direction. The first rotating direction is a clockwise direction, and the second rotating direction is a counterclockwise direction, for example. The angle of rotation of the stage 2 and the analysis unit 100 is described in detail below.

The washing device 1 may include a head driver 4, and the controller 30 may include a head controller 34. The head controller 34 controls the head driver 4 so as to bring the nozzle head 13 to be closer to or away from the stage 2. The stage controller 31 then controls the stage driver 3 so as to allow the stage 2 and the analysis unit 100 mounted on the stage 2 to rotate at a predetermined angle in the first direction or in the second direction.

The cleaning solution container 16 is used for storing a cleaning solution CS. The cleaning solution CS may be pure water. The dispensing controller 32 controls the cleaning solution dispensing driver 14 so as to supply the cleaning solution CS stored in the cleaning solution container 16 to the nozzle head 13. In the state in which the analysis unit 100 and the nozzle head 13 are close to each other, the cleaning solution CS is dispensed from the dispensing nozzle 11 into the wells 130.

The suction controller 33 controls the cleaning solution suction driver 15 so as to suck the cleaning solution CS dispensed to the wells 130 with the suction nozzle 12. The cleaning solution CS sucked from the wells 130 is stored in the waste liquid container 17. The waste liquid container 17 is used for storing a waste liquid WL. The cleaning solution dispensing driver 14 and the cleaning solution suction driver 15 may each be a pump.

A washing method according to one or more embodiments is described below with reference to FIG. 8 to FIG. 14. The washing method described below is in particular an example of a method of washing the wells 130. FIG. 9 and FIG. 11 to FIG. 13 each schematically illustrate the flowing direction of the cleaning solution CS indicated by the arrows.

The efficiency of washing is typically improved in association with an increase in a flow rate of the cleaning solution CS. For example, the increase in the flow rate of the cleaning solution CS can efficiently remove detection target substances and nanoparticles fixed by non-specific binding to the analysis substrate 110. The flow rate of the cleaning solution CS is thus preferably increased during washing after fixing antibodies to the analysis substrate 110 and during washing after specifically binding detection target substances and antibodies together.

The increase in the flow rate of the cleaning solution CS during washing after specifically binding nanoparticles to detection target substances, however may lead the nanoparticles to come off due to the flow of the cleaning solution. The reason for easy separation of the nanoparticles is presumed to be that nanoparticles typically have a greater size or weight than antibodies and detection target substances. The flow rate of the cleaning solution CS is thus preferably decreased during washing after specifically binding the nanoparticles to the detection target substance.

The washing device 1 (particularly the controller 30) can choose whether to clean the wells 130 with the flow rate of the cleaning solution CS relatively increased or relatively decreased, in accordance with a predetermined program or an instruction by the operator.

A method of washing the wells 130 while relatively increasing the flow rate of the cleaning solution CS is described below with reference to the flowchart shown in FIG. 8 together with FIG. 9. The cleaning solution CS is stored in the cleaning solution container 16. The controller 30 chooses the method of washing the wells 130 with the flow rate of the cleaning solution CS relatively increased, in accordance with a predetermined program or an instruction by the operator. The following indications in parentheses refer to the case in which the head controller 34 controls the head driver 4 so as to bring the nozzle head 13 to be closer to or away from the stage 2.

Figure 8:
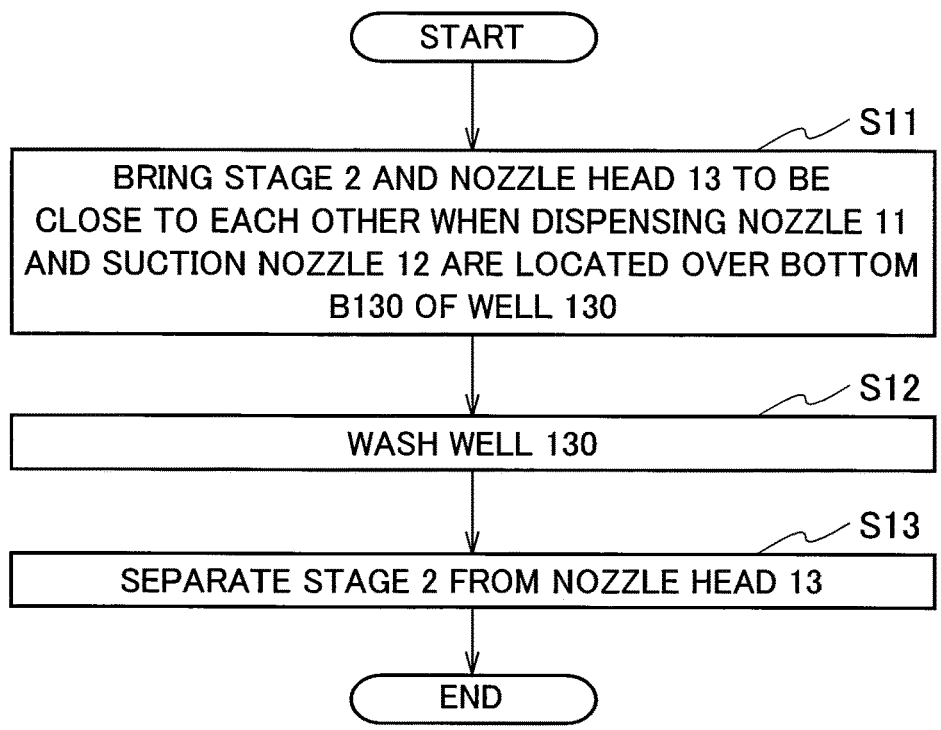
FIG. 8 is a flowchart illustrating a washing method according to one or more embodiments.

In step S11 of FIG. 8, in the state in which the stage 2 and the nozzle head 13 are aligned with each other (in the initial state), the stage controller 31 (the head controller 34) controls the stage driver 3 (the head driver 4) so as to bring the stage 2 and the nozzle head 13 to be close to each other.

Figure 9:
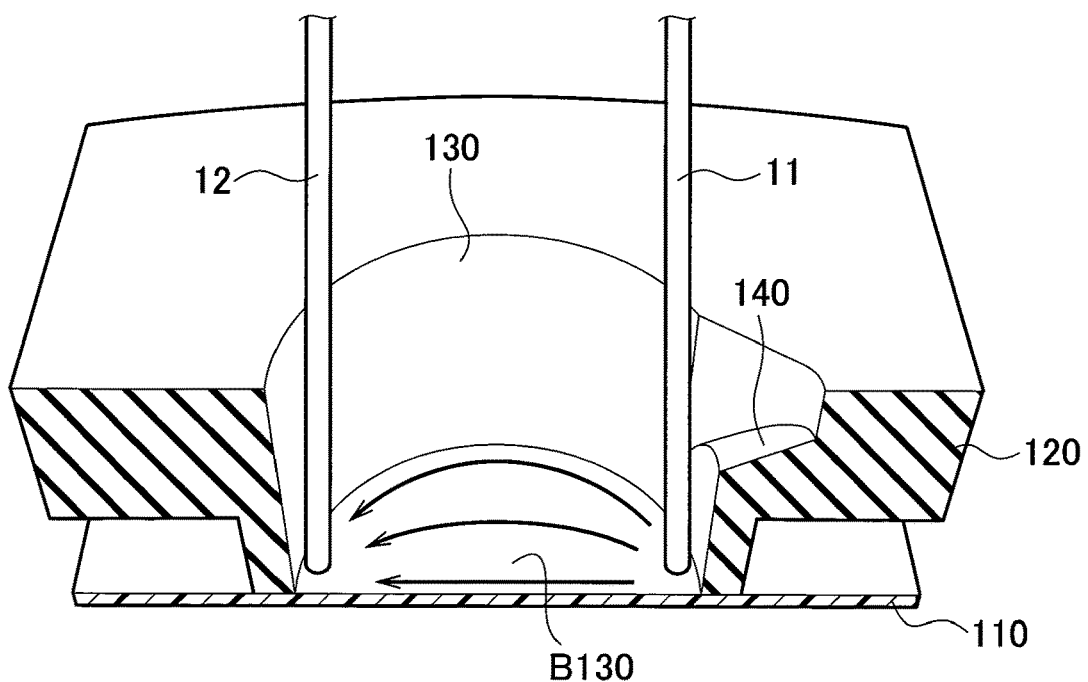
FIG. 9 is a view illustrating a positional relationship between the well, a dispensing nozzle, and a suction nozzle.

As shown in FIG. 9, the dispensing nozzle 11 and the suction nozzle 12 are inserted to the well 130 so that the respective tips are located close to the bottom B130 of the well 130. The expression "the state in which the stage 2 and the nozzle head 13 are aligned with each other" as used herein refers to a state in which the dispensing nozzle 11 and the suction nozzle 12 are located over the bottom B130 of the well 130.

In step S12, the dispensing controller 32 controls the cleaning solution dispensing driver 14 so as to dispense the cleaning solution CS stored in the cleaning solution container 16 to the well 130 through the dispensing nozzle 11. The suction controller 33 controls the cleaning solution suction driver 15 so as to suction the cleaning solution CS dispensed to the well 130 through the suction nozzle 12. The well 130 is thus cleaned with the cleaning solution CS.

During the washing of the well 130, the dispensing controller 32 and the suction controller 33 may execute the washing processing for a predetermined period of time for sucking the cleaning solution CS with the suction nozzle 12 while discharging the cleaning solution CS from the dispensing nozzle 11, or may execute the washing processing at predetermined times for sucking the cleaning solution CS remaining in the well 130 with the suction nozzle 12 after discharging the cleaning solution CS from the dispensing nozzle 11. The respective steps of the above washing processing may be combined together. The dispensing controller 32 and the suction controller 33 may repeat the washing processing in step S2 at predetermined times. The washing processing described above may be executed in accordance with a predetermined program or an instruction by the operator.

After finishing the washing of the well 130, the dispensing controller 32 and the suction controller 33 control the cleaning solution dispensing driver 14 and the cleaning solution suction driver 15 so as to stop dispensing the cleaning solution CS and then stop the suction of the cleaning solution CS. In step S13, the stage controller 31 (the head controller 34) controls the stage driver 3 (the head driver 4) so as to separate the stage 2 (the nozzle head 13) from the nozzle head 13 (the stage 2).

The suction controller 33 may control the cleaning solution suction driver 15 so as to stop the suction of the cleaning solution CS after the stage 2 (the nozzle head 13) is away from the nozzle head 13 (the stage 2). The well 130 thus can be cleaned with the flow rate of the cleaning solution CS relatively increased through the steps S11 to S13.

A method of washing the wells 130 while relatively decreasing the flow rate of the cleaning solution CS is described below with reference to the flowchart shown in FIG. 10 together with FIG. 11 to FIG. 13. The cleaning solution CS is stored in the cleaning solution container 16. The controller 30 chooses the method of washing the wells 130 with the flow rate of the cleaning solution CS relatively decreased, in accordance with a predetermined program or an instruction by the operator. The following indications in parentheses refer to the case in which the head controller 34 controls the head driver 4 so as to bring the nozzle head 13 to be closer to or away from the stage 2.

Figure 10:
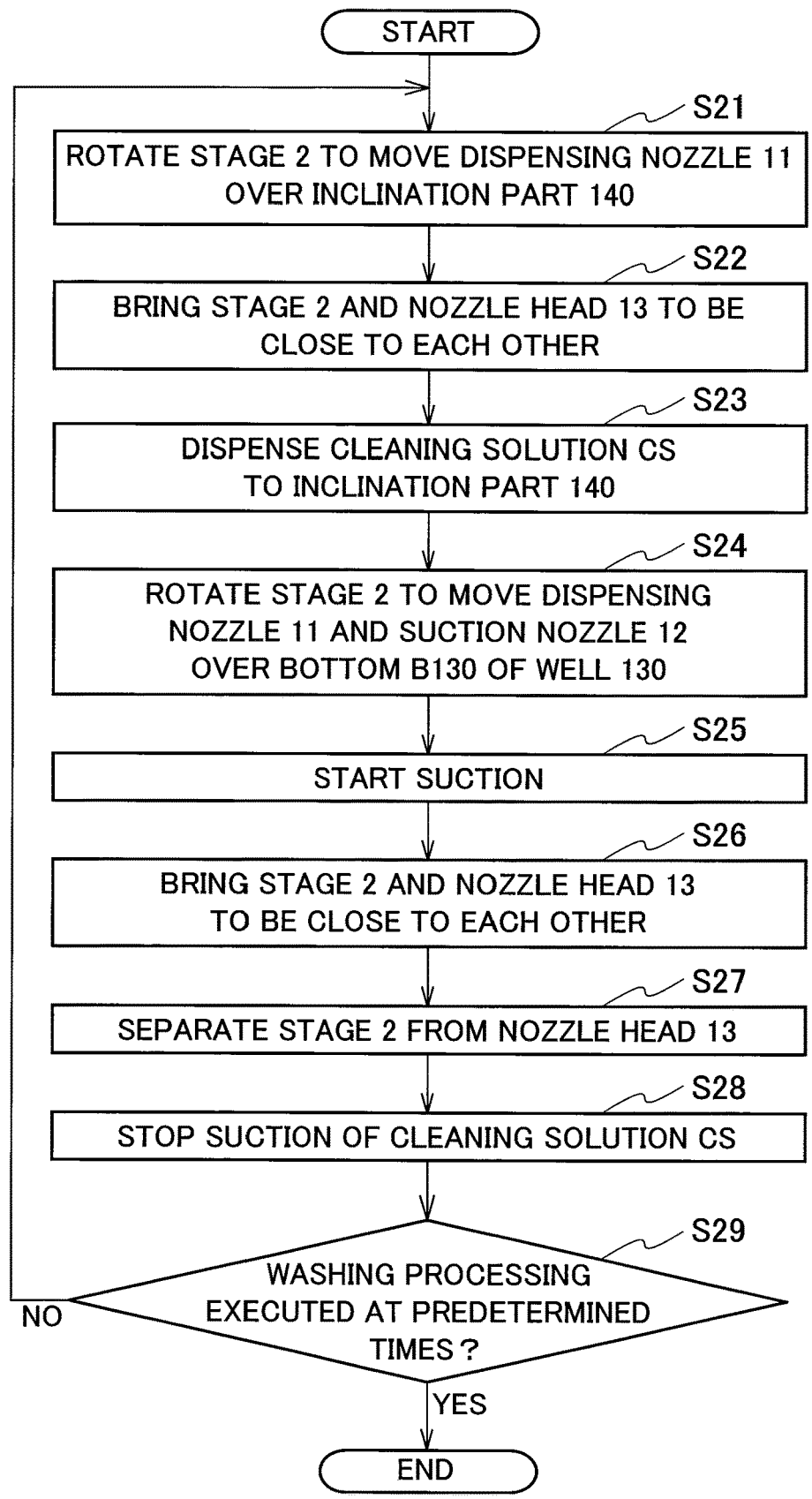
FIG. 10 is a flowchart illustrating the washing method according to one or more embodiments.

In step S21 of FIG. 10, the stage controller 31 controls the stage driver 3 so as to allow the stage 2 to rotate (move) at a predetermined angle in the first or second direction from the state in which the stage 2 and the nozzle head 13 are aligned with each other (in the initial state). When the analysis unit 100 has the configuration illustrated in FIG. 1, the stage controller 31 controls the stage driver 3 so as to allow the stage 2 to rotate at a predetermined angle in the second rotating direction (in the counterclockwise direction).

Figure 11:
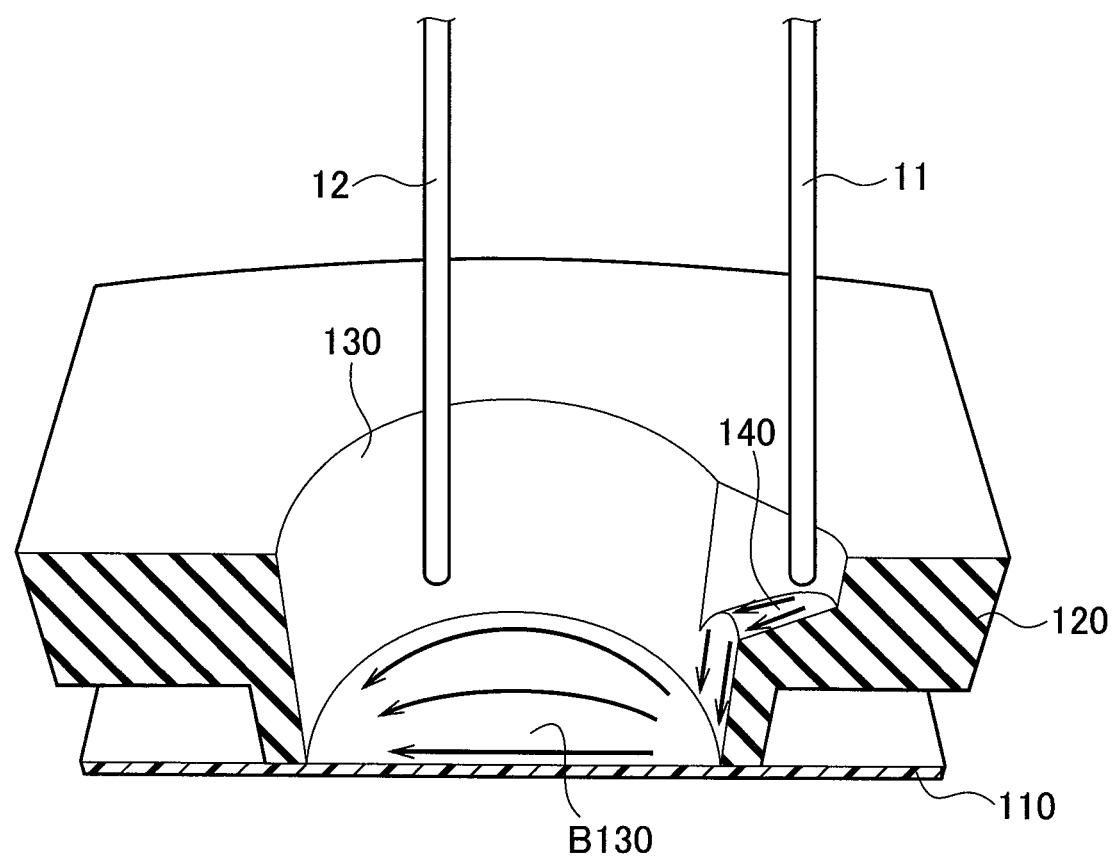
FIG. 11 is a view illustrating a positional relationship between the dispensing nozzle and an inclination part.
Figure 12:
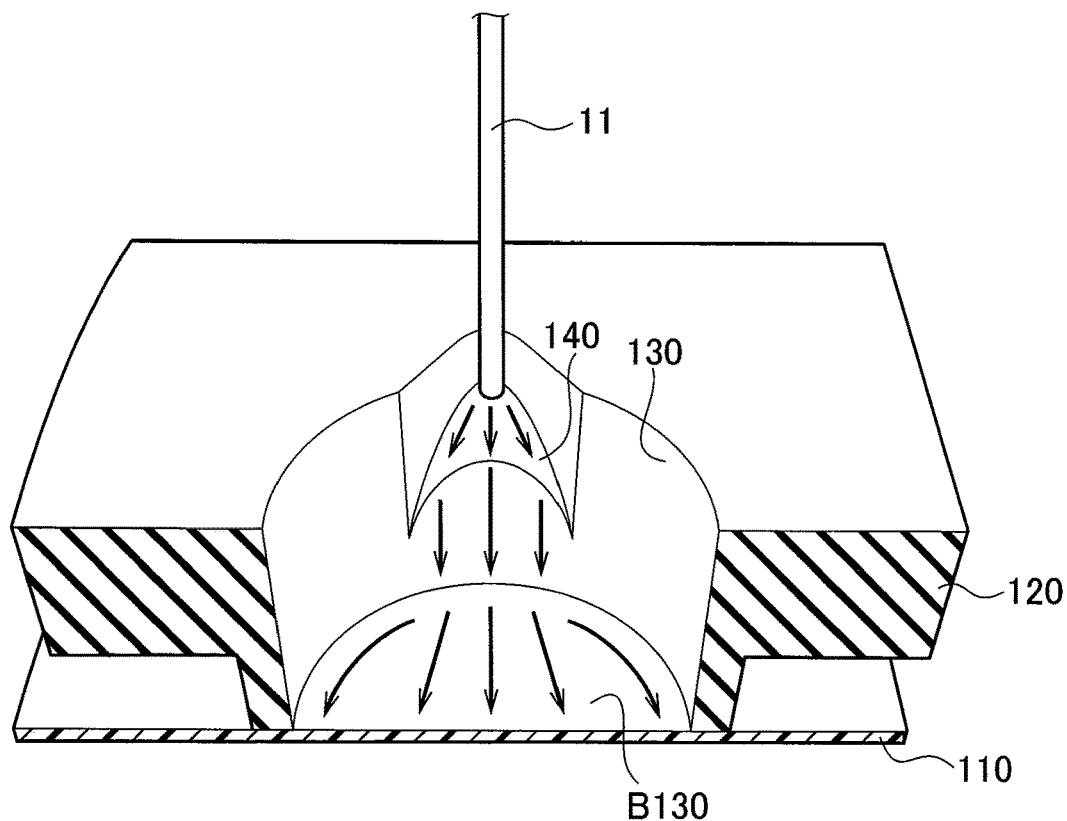
FIG. 12 is a view illustrating a positional relationship between the dispensing nozzle and the inclination part.

The dispensing nozzle 11 is then moved to a position over the inclination part 140, as illustrated in FIG. 11. In particular, the stage controller 31 controls the stage driver 3 so as to move the dispensing nozzle 11 over the inclination part 140. The state in which the dispensing nozzle 11 is located over the inclination part 140 may be set as the initial state. Setting as the initial state can eliminate the step S21.

In step S22, the stage controller 31 (the head controller 34) controls the stage driver 3 (the head driver 4) so as to bring the stage 2 and the nozzle head 13 to be close to each other. As illustrated in FIG. 11 or FIG. 12, the dispensing nozzle 11 is inserted to the well 130 so that the tip is located close to the inclination part 140 (particularly the middle of the inclination part 140).

In step S23, the dispensing controller 32 controls the cleaning solution dispensing driver 14 so as to dispense the cleaning solution CS stored in the cleaning solution container 16 toward the inclination part 140 through the dispensing nozzle 11. The cleaning solution CS dispensed from the dispensing nozzle 11 spreads over the inclination part 140 in the width direction due to its inclination, and further flows along the inner circumferential surface P130 of the well 130 to reach the bottom B130. The cleaning solution CS dispensed from the dispensing nozzle 11 toward the inclination part 140 thus flows into the well 130, namely, the dispensing controller 32 causes the cleaning solution CS to be dispensed toward the inclination part 140 through the dispensing nozzle 11 so as to be poured into the well 130. The dispensing controller 32 controls the cleaning solution dispensing driver 14 so as to stop dispensing the cleaning solution CS at a point when a predetermined amount of the cleaning solution CS has been dispensed or the cleaning solution CS has been dispensed for a predetermined period of time.

The inclination part 140 can regulate the flow rate of the cleaning solution CS depending on the degree of inclination in the radial direction or the circumferential direction of the well 130, or depending on the degree of spread of the width. The inclination part 140 thus serves as a flow rate regulation unit for regulating the flow rate of the cleaning solution CS.

In step S24, the stage controller 31 controls the stage driver 3 so as to allow the stage 2 to rotate (move) at a predetermined angle in the direction opposite to the rotating direction in step S21. When the analysis unit 100 has the configuration illustrated in FIG. 1, the stage controller 31 controls the stage driver 3 so as to allow the stage 2 to rotate at a predetermined angle in the first rotating direction (in the clockwise direction).

The dispensing nozzle 11 and the suction nozzle 12 are then moved to a position so that the respective tips are located over the bottom B130 of the well 130. In particular, the stage controller 31 controls the stage driver 3 so as to move the dispensing nozzle 11 and the suction nozzle 12 over the bottom B130 of the well 130.

In step S25, the suction controller 33 controls the cleaning solution suction driver 15 so as to start the suction of the cleaning solution CS through the suction nozzle 12. In step S26, the stage controller 31 (the head controller 34) controls the stage driver 3 (the head driver 4) so as to bring the stage 2 and the nozzle head 13 to be much closer to each other.

Figure 13:
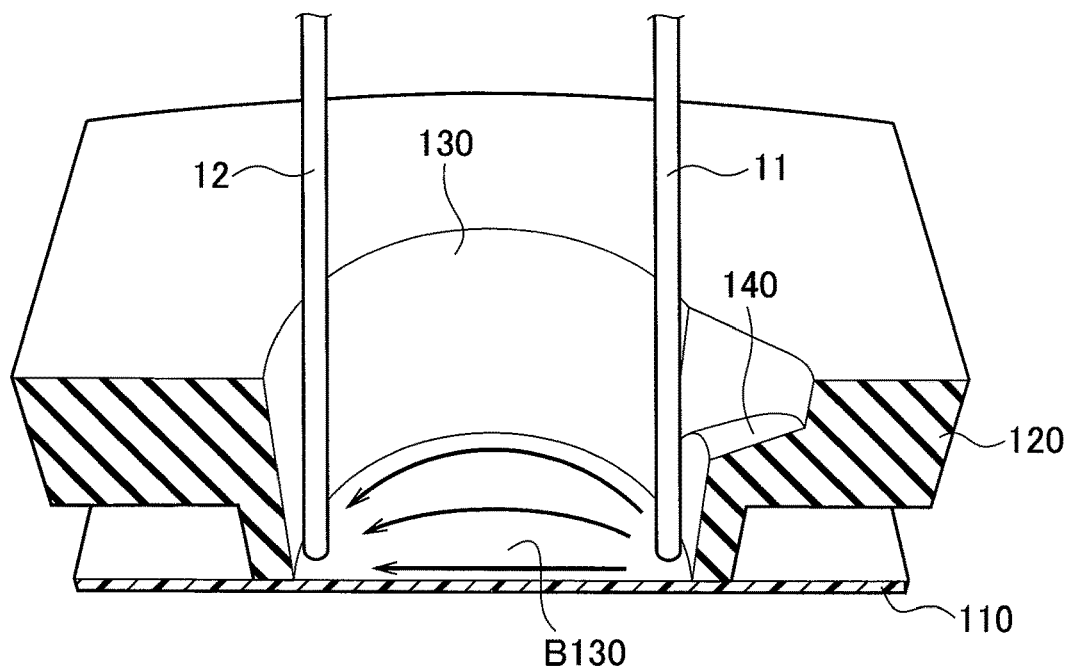
FIG. 13 is a view illustrating a positional relationship between the well, the dispensing nozzle, and the suction nozzle.

As illustrated in FIG. 13, the tips of the dispensing nozzle 11 and the suction nozzle 12 are located close to the bottom B130 of the well 130. Namely, the stage controller 31 (the head controller 34) controls the stage driver 3 (the head driver 4) so as to bring the tips of the dispensing nozzle 11 and the suction nozzle 12 to be located close to the bottom B130 of the well 130. The cleaning solution CS dispensed to the well 130 is sucked through the suction nozzle 12.

In step S27, the stage controller 31 (the head controller 34) controls the stage driver 3 (the head driver 4) so as to separate the stage 2 (the nozzle head 13) from the nozzle head 13 (the stage 2).

In step S28, the suction controller 33 controls the cleaning solution suction driver 15 so as to stop the suction of the cleaning solution CS. The well 130 thus can be cleaned with the flow rate of the cleaning solution CS relatively decreased through the steps S21 to S28. The washing processing from step S21 to step S28 may be repeated at predetermined times. The washing processing described above is executed in accordance with a predetermined program or an instruction by the operator.

In step S29, the controller 30 determines whether the washing processing, when determined to be repeated, has been executed at predetermined times. When the washing processing has not been repeated at predetermined times (NO), the washing device returns the process to step S21. When the washing processing has been repeated at predetermined times (YES), the washing device 1 finishes the washing processing.

Figure 14:
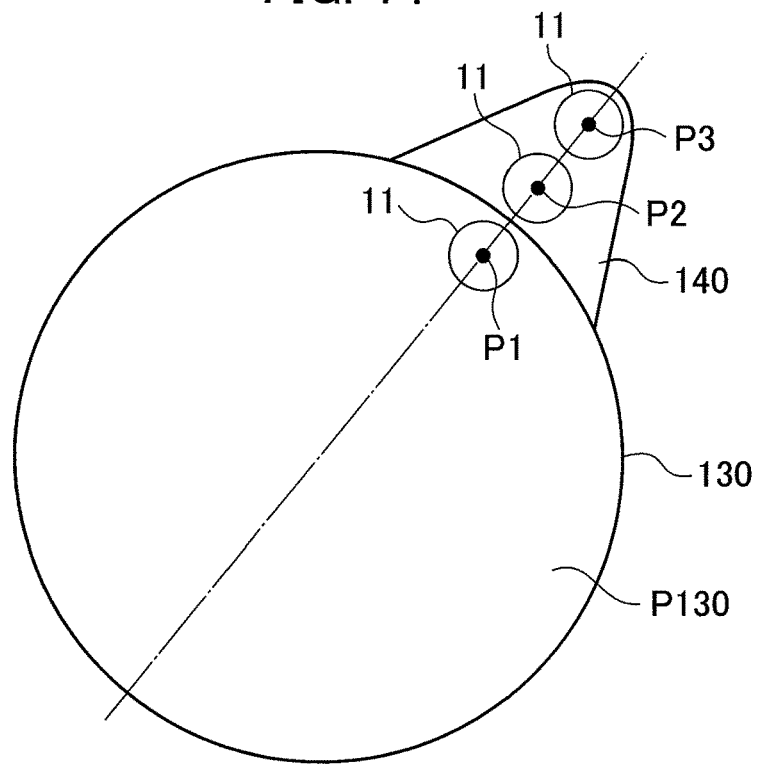
FIG. 14 is a view illustrating a positional relationship between the dispensing nozzle, the well, and the inclination part.

FIG. 14 is a diagram illustrating a positional relationship between the dispensing nozzle 11, the bottom B130 of the well 130, and the inclination part 140. The controller 30 can move the dispensing nozzle 11 to any of positions P1 to P3 in accordance with a predetermined program or an instruction by the operator. In particular, the stage controller 31 controls the stage driver 3 so as to rotate the analysis unit 100 mounted on the stage 2 by an angle selected from predetermined angles in the first or second direction. While the position P1, the position P2, and the position P3 are located actually on curves (arcs) along the rotating direction of the analysis unit 100, the respective positions P1, P2, and P3 can be located on the straight line as shown in FIG. 14.

When the analysis unit 100 has the configuration illustrated in FIG. 1, the stage controller 31 controls the stage driver 3 so as to rotate the stage 2 by a first angle in the first rotating direction. This rotation can move the dispensing nozzle 11 from the first position P1 to the second position P2. The stage controller 31 controls the stage driver 3 so as to rotate the stage 2 by a second angle in the first rotating direction. This rotation can move the dispensing nozzle 11 from the first position P1 to the third position P3. The stage controller 31 may control the stage driver 3 to rotate the stage 2 by a third angle in the first rotating direction so as to move the dispensing nozzle 11 from the second position P2 to the third position P3.

The cleaning solution CS dispensed from the dispensing nozzle 11 at the first position P1 can have a relatively large flow rate. The dispersion degree of pressure of the cleaning solution CS dispensed from the dispensing nozzle 11 thus can be regulated according to the dispensing position in the inclination part 140 in the radial direction of the well 130. Namely, the cleaning solution CS dispensed from the dispensing nozzle 11 at the third position P3 can have a relatively small flow rate.

The cleaning solution CS dispensed from the dispensing nozzle 11 can have a smaller flow rate at the second position P2 than at the first position P1, and can have a larger flow rate at the second position P2 than at the third position P3. The dispersion degree of pressure of the cleaning solution CS dispensed from the dispensing nozzle 11 can be regulated according to the dispensing position in the inclination part 140 in the radial direction of the well 130. The regulation of the pressure dispersion can regulate the flow rate of the cleaning solution CS according to the dispensing position in the inclination part 140 in the radial direction of the well 130 accordingly.

It should be understood that the present invention is not intended to be limited to one or more embodiments described above, and various modifications will be apparent to those skilled in the art without departing from the scope of the present invention.

Figure 15:
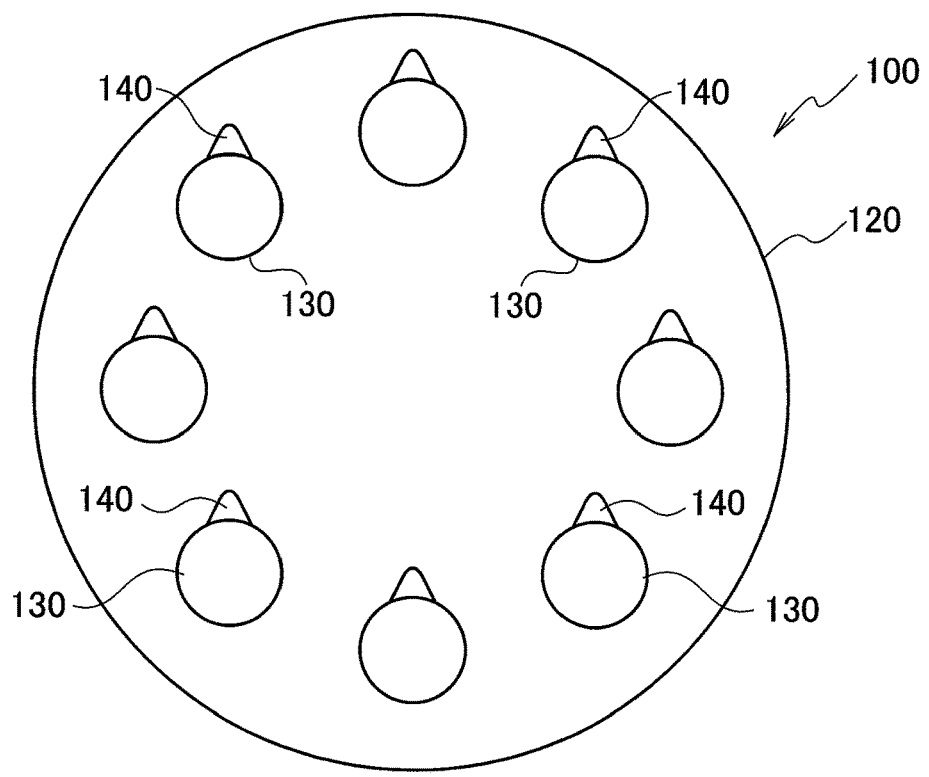
FIG. 15 is a plan view illustrating a configuration of an analysis unit.

As illustrated in FIG. 15, the analysis unit 100 may have a configuration in which all of the inclination parts 140 are arranged to face in the same direction in the wells 130. FIG. 15 illustrates the case in which the respective inclination parts 140 are arranged on the upper side of the wells 130. In this case, the stage controller 31 controls the stage driver 3 so as to move the stage 2 on which the analysis unit 100 is mounted downward by a predetermined distance. This can adjust the dispensing position of the cleaning solution CS, so as to regulate the flow rate of the cleaning solution CS accordingly. The respective inclination parts 140 are not necessarily arranged on the upper side of the wells 130, and are only required to face in the same direction in the wells 130.

Figure 16:
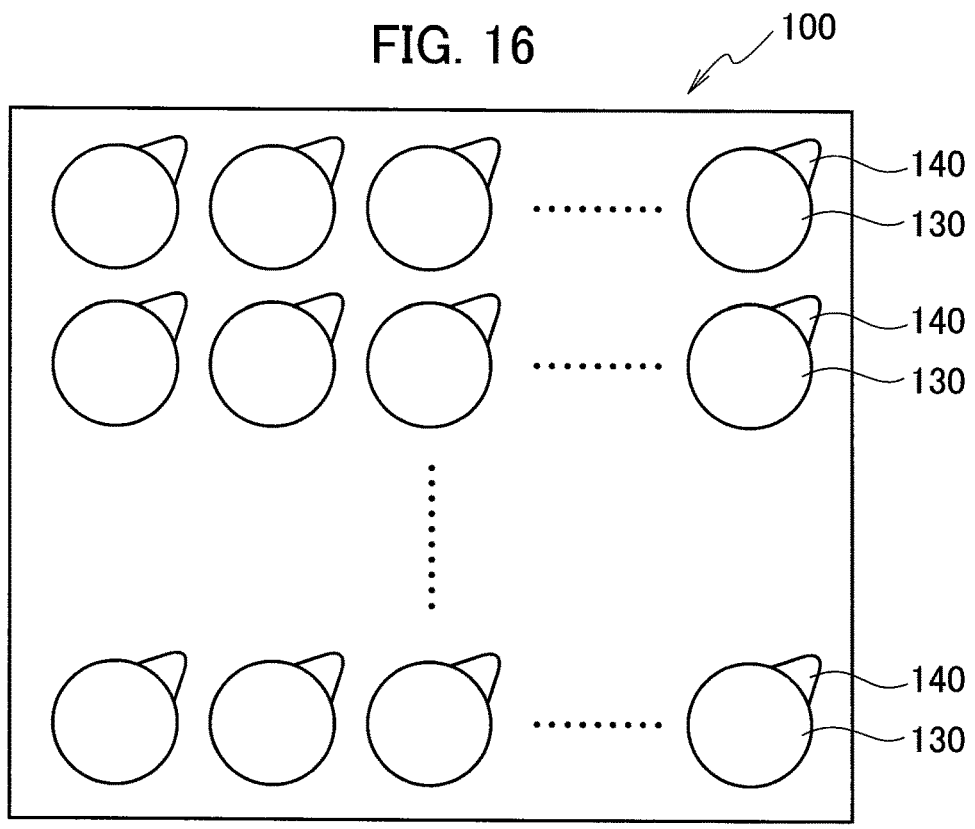
FIG. 16 is a plan view illustrating a configuration of an analysis unit.

The analysis unit 100 (with the cartridge 120 fitted to the analysis substrate 110) is not limited to the shape shown in FIG. 1. As illustrated in FIG. 16, the analysis unit 100 may have a cuboidal shape or may have any other shape. The plural wells 130 may be arranged along a straight line, or may be arranged in a matrix form including first straight lines and second straight lines perpendicular to the first straight lines as illustrated in FIG. 16.

Figure 17:
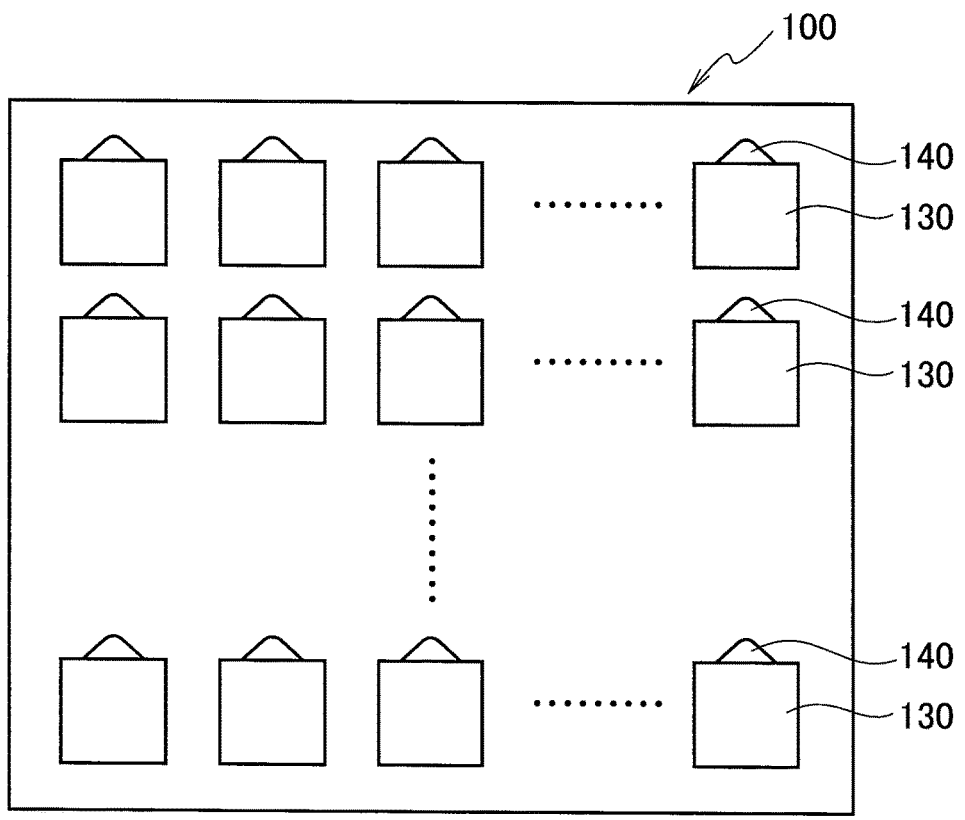
FIG. 17 is a plan view illustrating a configuration of an analysis unit.

The wells 130 (the penetration holes 121) are not limited to the shape shown in FIG. 1. As illustrated in FIG. 17, the wells 130 may have a rectangular shape in a planar pattern or may have any other shape.

According to the analysis unit 100, the washing device 1, and the washing method of one or more embodiments, the analysis unit 100 includes the inclination parts 140 connected to the wells 130. The washing device 1 moves the dispensing nozzle 11 over the inclination part 140 so as to dispense the cleaning solution CS toward the inclination part 140 from the dispensing nozzle 11. The cleaning solution CS flows into the well 130 while the pressure is dispersed by the inclination part 140.

According to the analysis unit 100, the washing device 1, and the washing method of one or more embodiments, discharging the cleaning solution CS to the wells 130 via the inclination parts 140, or adjusting the position in the inclination parts 140 from which the cleaning solution CS is dispensed, can regulate the flow rate of the cleaning solution CS for washing the wells 130.

While one or more embodiments have exemplified the case of discharging a cleaning solution, the present invention can also be applied to a case of discharging any type of solution such as a buffer solution including antibodies or nanoparticles, and a sample solution including or having a probability of including detection target substances. A cleaning solution, a buffer solution, and a sample solution are collectively referred to herein as a solution.

What is claimed is:
1. An analysis unit for quantitating detection target substances bound to antibodies, the analysis unit comprising:
   a well having a hole-like shape defined by an opening, an inner circumferential surface, and a bottom; and
   an inclination part comprising a saddle-like portion provided, at least in part, in a circumferential direction of the well, the saddle-like portion protruding outward in a radial direction of the well,
   wherein an inner circumferential surface side of the saddle-like portion connects to the inner circumferential surface,
   wherein the saddle-like portion is inclined in such a way that a height of the saddle-like portion with respect to the bottom decreases from an outer end portion to an inner circumferential surface side in the radial direction of the saddle-like portion,
   wherein the saddle-like portion is further inclined in such a way that a height of the saddle-like portion with respect to the bottom decreases from a center portion to both outer portions in the circumferential direction of the saddle-like portion, wherein the bottom is a part of an analysis substrate provided with a track region including convex portions and recesses alternately arranged, and wherein a cartridge is provided with a plurality of pairs of the opening and the inner circumferential surface.

2. A washing device comprising:

a stage on which an analysis unit is mounted;

a dispensing nozzle from which a solution is injected to the well;

a nozzle head to which a suction nozzle for sucking the solution in the well and the dispensing nozzle are fixed; and a controller configured to control the stage or the dispensing nozzle so as to bring the dispensing nozzle to be closer to or away from the saddle-like portion, and control the dispensing nozzle to dispense the solution to the inclined surface, wherein the analysis unit comprising:

a well having a hole-like shape defined by an opening, an inner circumferential surface, and a bottom; and an inclination part comprising a saddle-like portion provided, at least in part, in a circumferential direction of the well, the saddle-like portion protruding outward in a radial direction of the well, wherein an inner circumferential surface side of the saddle-like portion connects to the inner circumferential surface, wherein the saddle-like portion is inclined in such a way that a height of the saddle-like portion with respect to the bottom decreases from an outer end portion to an inner circumferential surface side in the radial direction of the saddle-like portion, wherein the saddle-like portion is further inclined in such a way that a height of the saddle-like portion with respect to the bottom decreases from a center portion to both outer portions in the circumferential direction of the saddle-like portion, and wherein the controller controls the nozzle head or the stage so as to bring the dispensing nozzle to be closer to or away from the saddle-like portion, controls the dispensing nozzle so as to dispense the solution to the inclination part, and controls the suction nozzle so as to suck the solution in the well.

3. A washing method using the washing device of claim 2, the method comprising:

causing the controller of the analysis unit of claim 1 to control a stage on which the analysis unit is mounted, so as to bring a dispensing nozzle to be located over the inclination part of the analysis unit;

causing the controller to control the dispensing nozzle so as to dispense a solution to the inclination part; and causing the controller to control a suction nozzle so as to suck the solution flowing into the well through the inclination part.

* * * * *